United States Patent [19]

Sussman

[11] Patent Number: 4,941,227
[45] Date of Patent: Jul. 17, 1990

[54] DEVICE FOR CLEANING DENTAL IMPLANT POSTS

[76] Inventor: Harold I. Sussman, 64 Popham Rd., Scarsdale, N.Y. 10583

[21] Appl. No.: 302,025

[22] Filed: Jan. 25, 1989

[51] Int. Cl.⁵ ............................................. D46B 9/04
[52] U.S. Cl. .................................. 15/167.1; 15/167.2; 15/160; 15/206; 15/207
[58] Field of Search .................... 15/167.1, 167.2, 160, 15/164, 206, 207

[56] References Cited

U.S. PATENT DOCUMENTS

| | | | |
|---|---|---|---|
| 229,823 | 7/1980 | Holz et al. | 15/167.2 |
| 1,133,930 | 3/1915 | Carroll | 15/167.2 |
| 1,195,190 | 8/1916 | Dunlap . | |
| 1,337,819 | 4/1920 | Braun . | |
| 1,812,626 | 6/1931 | Edison | 15/167.1 |
| 2,070,603 | 8/1937 | Booth | 15/167.2 |
| 2,650,384 | 9/1953 | McClaskey . | |
| 3,559,226 | 2/1971 | Burns . | |
| 3,677,264 | 7/1972 | Brockman . | |
| 3,720,975 | 3/1973 | Nelson . | |
| 3,939,520 | 2/1976 | Axelsson . | |
| 4,053,959 | 10/1977 | Wiley . | |
| 4,222,143 | 9/1980 | Tarrson et al. . | |
| 4,319,377 | 3/1982 | Tarrson et al. . | |
| 4,375,115 | 3/1983 | Zimmerman | 15/210 R |
| 4,387,479 | 6/1983 | Kigyos . | |

FOREIGN PATENT DOCUMENTS 117317 1/1927 France .
704414 2/1931 France .
8281 7/1896 Sweden .
24259 of 1898 United Kingdom .

Primary Examiner—Frankie L. Stinson
Attorney, Agent, or Firm—Frishauf, Holtz, Goodman & Woodward

[57] ABSTRACT

A device for cleaning dental implant posts, includes a handle for grasping the device; and a brush secured to one end of the handle. The brush includes (i) a first flexible, springy resilient wire or plastic member secured to the one end of the handle and having a substantially part-circular configuration extending over an arc greater than 90° and less than 180°, the first member having a first inturned free end, (ii) a second flexible, springy resilient wire or plastic member secured to the same end of the handle and having a substantially part-circular configuration extending over an arc greater than 90° and less than 180°, the second member having a second inturned free end in opposing and at least partially facing relation to the first inturned free end so as to define a gap between the first and second inturned free ends which is smaller than the distance between proximal and distal sides of an implant post to be cleaned; and (iii) a plurality of circumferentially arranged bristles secured to each wire or plastic member. The first and second members may be made as a single unitary wire member.

20 Claims, 1 Drawing Sheet

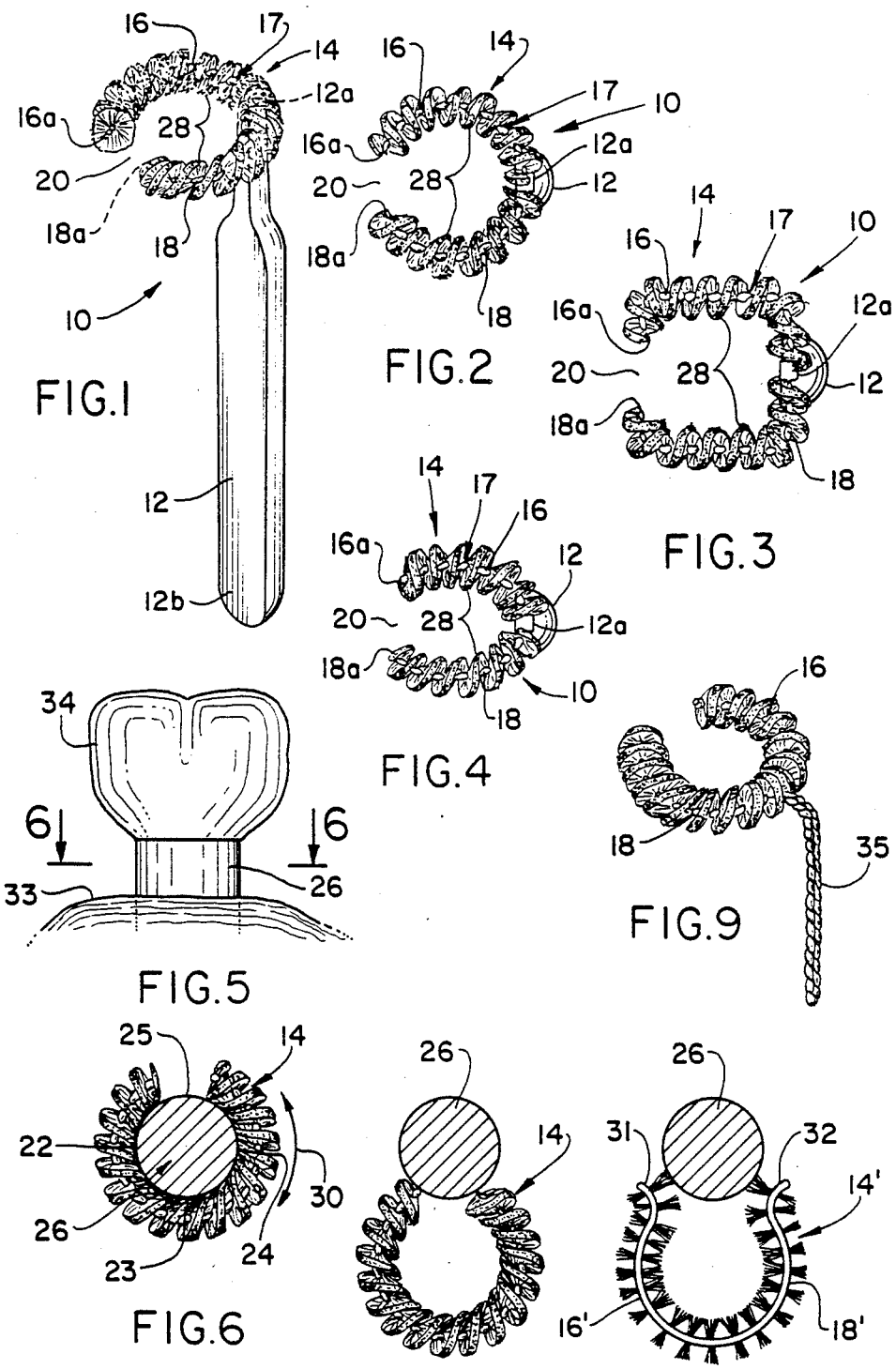

DEVICE FOR CLEANING DENTAL IMPLANT POSTS

BACKGROUND OF THE INVENTION

This invention relates generally to dental cleaning apparatus, and more particularly, is directed to a device for cleaning dental implant posts.

Surgery to secure dental implants to the jaw bone of a patient has recently become technically and economically available. The use of such dental implants is generally more desirable than so-called "false teeth" which are temporarily adhered to the gum surface. This is because the dental implants are permanently secured in the mouth of the patient.

Generally, surgery for such dental implants starts by making an incision in the gum of the patient to expose the bone over the site of the implant. A special drill then drills into the bone and the implant is screwed into place. The implant is covered for three to six months to permit undisturbed healing. Thereafter, the top of the implant is exposed and a post is attached. A bridge is then secured on the post and functions in the same manner as a natural tooth.

It will be appreciated that a portion of the post is generally accessible under the bridge. Thus, as with natural teeth, it is necessary to clean the bridge and post, particularly near and at the gum line.

Various types of tooth cleaning brushes have been proposed. Most of such brushes provide a single wire element or the like having bristles thereon which are adapted to clean the extremities of the teeth and enter the interproximal areas between teeth. Brushes of this type are shown, for example, in U.S. Pat. Nos. 3,559,226; 3,720,975; 3,939,520; 4,053,959; 4,222,143; and 4,319,377; 4,387,479. However, with these brushes, only one side of a tooth can be cleaned at any given time. In other words, the proximal, distal, buccal and lingual sides of the tooth must be cleaned separately. This requires a relatively large amount of time, and accordingly, the user may not take the time to carefully clean all of the tooth surfaces. Further, with such brushes, it would be difficult to use the same to clean all exposed surfaces of an implant post, particularly toward the lingual side. In addition, there is a tendency for a single pronged straight brush to bend away from the mesial and distal midpoint interproximal surfaces, thereby making cleaning even more difficult.

U.S. Pat. No. 3,677,264 discloses a toothbrush having two parallel and rotatable, generally conically shaped tooth and gum engaging implements. However, it is clear that this toothbrush could not be used to clean the proximal and distal sides of a tooth, let alone an implant post.

In the art of general brushing and scrubbing implements, devices are known having parallel wire elements with bristles thereon. Examples of such devices are shown in U.S. Pat. Nos. 1,195,190 and 1,337,819; British Patent No. 24,259; French Patent Nos. 117,317 and 704,414; and Swedish Patent No. 8,281. In the first place, these devices are not intended for the cleaning of teeth and could not be used as such. Further, the use of parallel wire elements would not enable a person to clean the lingual side of an implant post, along with the remaining sides, in a single cleaning motion.

Although French Patent No. 117,317 does disclose the use of one wire element being bent at its free end, it is noted that this Patent only envisions the use of one wire element at a time, the other wire element being removed from the device. In any event, a complete cleaning of an implant post could not be achieved in a single motion with this device.

Finally, French patent No. 24,259, although disclosing various bent wires, provides that the free ends of the wires are always parallel or slightly bent outwardly away from each other. Accordingly, complete cleaning of all implant post (or tooth) surfaces with a single motion could not be achieved with this brush.

OBJECTS OF THE INVENTION

It is an object of the present invention to provide a device for cleaning dental implant posts that overcomes the problems in the prior art.

It is another object of the present invention to provide a device for cleaning dental implant posts in which all post surfaces can be cleaned with a single cleaning motion.

It is still another object of the present invention to provide a device for cleaning dental implant posts in which lingual, buccal, proximal and distal sides of an implant post can be cleaned with a single cleaning motion.

It is yet another object of the present invention to provide a device for cleaning dental implant posts that is easy and economical to use and manufacture.

The above and other objects, features and advantages of the present invention will become readily apparent from the following detailed description which is to be read in connection with the accompanying drawings.

SUMMARY OF THE INVENTION

In accordance with an aspect of the present invention, a device for cleaning dental implant posts includes handle means for grasping the device; and brushing means secured to one end of the handle means, the brushing means including (i) a first flexible, resilient member secured to the one end of the handle means and having a convex configuration, the first member having a first inturned free end, (ii) a second flexible, resilient member secured to the one end of the handle means and having a convex configuration, the second member having a second inturned free end in opposing and at least partially facing relation to the first inturned free end so as to define a gap between the first and second inturned free ends which is smaller than the distance between proximal and distal sides of an implant post to be cleaned, and (iii) a plurality of inwardly directed bristles secured to each of said first and second members.

In a preferred arrangement the first and second members are integrally formed as a single unit, preferably of a springy wire or plastic material.

BRIEF DESCRIPTION OF THE DRAWINGS

FIG. 1 is a perspective view of a device for cleaning dental implant posts according to the present invention;

FIG. 2 is a top plan view of the device of FIG. 1;

FIG. 3 is a top plan view of a device according to another embodiment of the present invention;

FIG. 4 is a top plan view of a device according to yet another embodiment of the present invention;

FIG. 5 is a side elevational view of a side of a tooth implant with post with which the present invention is used;

FIG. 6 is a cross-sectional view, along line 6—6 of FIG. 5, showing the device of FIG. 1 used to clean the post 26;

FIG. 7 is a cross-sectional view of the post of FIG. 5, showing the start of operation of the device of FIG. 1 for wrapping around the implant post;

FIG. 8 shows a modified device of the present invention; and

FIG. 9 shows a perspective view of a further modified device of the present invention.

DETAILED DESCRIPTION

Referring to the drawings, a device 10 according to one embodiment of the present invention for cleaning dental implant screws or posts (hereinafter generally referred to as "post") includes an elongated handle 12 with which a person can grasp device 10. A brush member 14 is secured to on end 12a of handle 12 by means of adhesive or any other suitable securing means, while the user grasps the opposite end 12b of handle 12.

Brush member 14 includes first and second flexible, resilient, springy, wire members 16 and 18 secured to end 12a of handle 12, wire members 16, 18 each having a convex configuration. In this regard, each of the wire members 16, 18 can have a substantially part-circular configuration extending over an arc greater than 90° and less than 180°, as shown in FIG. 1. Alternatively, wire members 16, 18 can each have a substantially U-shaped configuration, as shown in FIG. 3 or a generally oval shape as shown in FIG. 4. Other suitable shapes could be used. In any case, first wire member 16 has a first inturned or inwardly directed free end 16a, and second wire member 18 has a second inturned or inwardly directed free end 18a.

In the embodiments of FIGS. 1, 3 and 4, it is preferable that wire members 16 and 18 be formed from a single, continuous, integral wire member 17 extending over an arc greater than 180°.

It will be appreciated that because first and second wire members 16 and 18 have mirror image convex configurations, the second inturned or inwardly directed free end 18a of wire portion 18 is in opposing and at least partially facing relation to first inturned free end 16a of wire portion 16 so as to define a gap 20 therebetween. The size of gap 20 is smaller than the distance between proximal and distal sides 22 and 24 (see FIGS. 5 and 6) of an implant post 26 to be cleaned.

Further, brush member 14 includes a plurality of bristles 28 secured to each wire member 16 and 18. The brush member 14 can be a twisted wire brush, such as shown in U.S. Pat. No. 3,559,226 or 4,319,377, for example. Although it is only necessary from the standpoint of the present invention to provide inwardly directed bristles 28, it is preferable that bristles 28 extend circumferentially around each wire member 16 and 18 at any point thereon. In this manner, the gingival surface and adjacent tooth surfaces will also be cleaned.

In use, as shown in FIG. 7, and with respect to the embodiment of FIG. 1, inturned ends 16a and 18a are moved into contact with the buccal side 23 of a post 26. Upon application of a force toward the lingual side 25 of post 26, wire members 16 and 18 are resiliently forced apart and around post 26 and "spring" back to the position shown in FIG. 6. Thereafter, all surfaces of post 26 are cleaned by moving brush member 14 only a small amount in the direction of double-headed arrow 30.

As shown in FIG. 8, the brush member 14', formed of members 16', 18', may be provided with outwardly turned free ends 31, 32 which serve as "camming" surfaces to facilitate sliding of the brush member 14 over the post 26. The free end portions 31, 32 may have bristles 28 thereon, or may be free of bristles, as desired. The modified device of FIG. 8 is shown as being made of plastic material, instead of wire members such as twisted wire members, to shown an alternate embodiment. Also, when the brush member 14', is made of plastic material, the camming surfaces 31, 32 may more easily slide over the post 26. The plastic material from which the brush member 14 is made can be any of the biologically safe springy plastic materials, such as polyethylene, polypropylene, or other suitable materials.

It will be appreciated that, with all of the embodiments of the invention, complete cleaning of all exposed surfaces of implant post 26 occurs with a single insertion of the post into the opening between the wire (or plastic) cleaning members, and with a single rotating or reciprocating cleaning motion over only a small angle in the direction of arrow 30 in FIG. 6. At the same time, gingival surface 33, the underside of tooth 34 and any adjacent tooth surfaces are also cleaned.

An important feature of the present invention is the spring action provided by the resilient wire or plastic members 16, 18. By virtue of the spring action provided by members 16, 18, the device effectively has a "memory" so that when the members 16, 18 are forced apart or deformed when passing around post 26, the member 16, 18 spring back to their initial positions to effectively wrap at least partly around the post 26 so as to provide excellent cleaning characteristics without the necessity of inserting the device from the lingual side.

The wire or plastic members 16, 18 may be integrally formed as a single member. Instead of the single unitary member adhered to the handle 12 in the manner shown in FIGS. 1–4, the members 16, 18 can have a connection member 35 extending therefrom, as shown in FIG. 9, and the elongated connecting member 35 may be connected to a handle member in a manner similar to that shown in any one of U.S. Pat. Nos. 4,387,479; 4,319,377; or 4,222,143; or in any other suitable manner. The connection member 30 is made of the same material (i.e., wire or plastic) as member 16, 18. Additionally, bristles are connected to the wire (i.e. twisted wire) member in the same manner as is known in the art, for example as shown by the above-mentioned patents, or as shown in U.S. Pat. No. 3,5559, 226, for example, or are embedded in plastic members 16, 18.

While the members 16, 18 were described above as being made of wire, preferably twisted wire with bristles thereon, they could be fabricated of any other suitable material, such as plastic material, having the bristle portions embedded therein or otherwise attached thereto. When made of plastic material, the material should be biologically safe for use in the mouth, and should have the necessary resiliency and spring characteristics so as to provide the springy action described hereinabove.

In a preferred embodiment, the implant screws or posts which are to be cleaned are generally around 4 mm, and range generally from between about 3.5 to about 4.5 mm in diameter. Preferably, the gap 20 is about 2.5 mm, and when the device is generally circular as shown in FIG. 2, the inner diameter of the circle (from wire-to-wire) should be about 4 mm or slightly less so as to provide a tight fit. If the bristles 28 are sufficiently stiff, the inner diameter of the "circle" formed by the members 16, 18 (FIG. 2) may be slightly larger than 4 mm, and the bristles will still give sufficient brushing against the rod or post to provide proper cleaning.

When the device is attached to a handle in the manner shown, for example, in U.S. Pat. Nos. 4,22,143; 4,319,377; or 4,387,479, the handle may be re-used and the wire member portion 14 can be made as a replaceable unit.

Having described specific preferred embodiments of the invention with reference to the accompanying drawings, it will be appreciated that the present invention is not limited to those precise embodiments, and that various changes and modifications may be effected therein by one of ordinary skill in the art without departing from the scope or spirit of the invention as defined in the appended claims.

What is claimed is:

1. A device for cleaning dental implant posts, said cleaning device comprising:
    (a) handle means for manually grasping said device; and
    (b) brushing means secured to one end of said handle means, said brushing means including:
        (i) a first flexible, resilient wire member portion secured to said one end of said handle means and having a convex configuration, said first wire member portion having a first inturned free end;
        (ii) a second flexible, resilient wire member portion secured to said one end of said handle means and having a convex configuration, said convex configurations of said first and second wire member portions facing each other, and said second wire member portion having a second inturned free end in opposing and at least partially facing relation to said first inturned free end so as to define a gap between said first and second inturned free ends which is smaller than the distance between proximal and distal sides and an implant post to be cleaned; and
        (iii) a plurality of inwardly directed bristles secured to each said wire member portion; and wherein
    (c) said first and second wire member portions and said bristles secured to each wire member portion are dimensioned so as to be received between adjacent teeth at least at the gingival area, and said bristles being arranged to brush a dental implant post supporting a tooth at the lingual surface, at the buccal surface and at the gingival margin adjacent the post, said wire portions and said bristles together engaging around a post over an arc greater than 180° and less than 360°; and
    said wire member portions are made of spring wire so that when said wire member portions are deflected or spread apart when passing over a post, the wire member portions resiliently return toward their original positions to extend around a major portion of the circumference of said post.

2. A device according to claim 1, wherein said first and second wire member portion are mirror images of each other.

3. A device according to claim 1, wherein said first wire member portion has a substantially part-circular configuration and extends over an arc greater than 90° and less than 180°.

4. A device according to claim 3, wherein said second wire member portion has a substantially part-circular configuration and extends over an arc greater than 90° and less than 180°.

5. A device according to claim 1, wherein said first and second wire member portions are integrally formed from a single wire element.

6. A device according to claim 1, wherein said first and second wire member portions each have a substantially U-shaped configuration.

7. A device according to claim 1, wherein said first and second wire member portions together define a generally oval shape.

8. A device according to claim 1, wherein said bristles are directed outwardly as well as inwardly, so as to also clean teeth adjacent to said posts.

9. A device according to claim 1, wherein said inturned free ends of said wire portions have outwardly directed camming surfaces to facilitate sliding over an implant past to be cleaned.

10. A device according to claim 1, wherein said wire members are twisted wire members.

11. A device for cleaning dental implant posts, said cleaning device comprising:
    (a) handle means for manually grasping said device; and
    (b) brushing means secured to one end of said handle means, said brushing means including:
        (i) a first flexible, resilient, spring-like member secured to said one end of said handle means and having a convex configuration, said first member having a first inturned free end;
        (ii) a second flexible, resilient, spring-like member secured to said one end of said handle means and having a convex configuration, said convex configurations of said first and second members facing each other, and said second member having a second inturned free end in opposing and at least partially facing relation to said first inturned free end so as to define a gap between said first and second inturned free ends which is smaller than the distance between proximal and distal sides of an implant post to be cleaned; and
        (iii) a plurality of inwardly directed bristles secured to each said members; and wherein
    (c) said first and second spring-like members and said bristles secured to each spring-like member are dimensioned so as to be received between adjacent teeth at least at the gingival area, and said bristles being arranged to brush a dental implant post supporting a tooth at the lingual surface, at the buccal surface and at the gingival margin adjacent the post, said spring-like members and said bristles together engaging around a post over an arc greater than 180° and less than 360°; and
    said spring-like members are resiliently yieldable so that when they are deflected or spread apart when passing over a post, they resiliently return toward their original positions to extend around a major portion of the circumference of said post.

12. A device according to claim 11, wherein said first and second members are mirror images of each other.

13. A device according to claim 11, wherein said first member has a substantially part-circular configuration and extends over an arc greater than 90° and less than 180°.

14. A device according to claim 13, wherein said second member has a substantially part-circular configuration and extends over an arc greater than 90° and less than 180°.

15. A device according to claim 11, wherein said first and second members are integrally formed as a single unitary member.

16. A device according to claim 11, wherein said first member has a substantially U-shaped configuration.

17. A device according to claim 16, wherein said second member has a substantially U-shaped configuration.

18. A device according to claim 11, wherein said first and second members together define a generally oval shape.

19. A device according to claim 11, wherein said bristles are directed outwardly as well as inwardly, so as to also clean teeth adjacent to said posts.

20. A device according to claim 11, wherein said inturned free ends of said first and second members have respective outwardly directed camming surfaces to facilitate sliding over an implant past to be cleaned.

* * * * *

UNITED STATES PATENT AND TRADEMARK OFFICE
CERTIFICATE OF CORRECTION

PATENT NO. : 4,941,227
DATED : July 17, 1990
INVENTOR(S) : Harold I. SUSSMAN

It is certified that error appears in the above-identified patent and that said Letters Patent is hereby corrected as shown below:

Title page, Section [56] "References Cited":

Change USP "2,070,603 8/1937 Booth" to

--2,090,663 8/1937 Booth--.

Signed and Sealed this

Seventh Day of July, 1992

Attest:

DOUGLAS B. COMER

*Attesting Officer*   *Acting Commissioner of Patents and Trademarks*